United States Patent [19]
Prasad et al.

[11] Patent Number: 6,034,245
[45] Date of Patent: Mar. 7, 2000

[54] PROCESS FOR MAKING 2-(METHYLTHIO)-5-(TRIFLUOROMETHYL)-1,3,4-THIADIAZOLE USING METHYLDITHIOCARBAZINATE WITH TRIFLUOROACETIC ACID WITH SELECTIVE REMOVAL OF 2,5-BIS (METHYLTHIO)-1,3,4-THIADIAZOLE

[75] Inventors: Vidyanatha A. Prasad, Leawood, Kans.; Thomas Schmidt, Haan, Germany; Peter E. Newallis, Leawood, Kans.

[73] Assignees: Bayer Corporation, Pittsburgh, Pa.; Bayer Aktiengesellschaft, Leverkusen, Germany

[21] Appl. No.: 09/215,492

[22] Filed: Dec. 18, 1998

Related U.S. Application Data

[63] Continuation-in-part of application No. 08/989,563, Dec. 12, 1997.

[51] Int. Cl.[7] .............................................. C07D 285/125
[52] U.S. Cl. .............................................................. 548/136
[58] Field of Search ............................................. 548/136

[56] References Cited

U.S. PATENT DOCUMENTS

| | | | |
|---|---|---|---|
| 3,562,284 | 2/1971 | Newman et al. | 260/302 |
| 4,988,380 | 1/1991 | Forster et al. | 71/90 |
| 5,101,034 | 3/1992 | Schmidt et al. | 548/136 |
| 5,147,443 | 9/1992 | Diehr et al. | 71/67 |
| 5,162,539 | 11/1992 | Diehr | 548/136 |
| 5,177,090 | 1/1993 | Diehr et al. | 514/363 |

OTHER PUBLICATIONS

Gyoefi and Csavassy, Acta Chimica Academiae Scientiarum Hungaricae, Tomus 82 (1): 91–97, (month unavailable) 1974.

*Primary Examiner*—Robert Gerstl
*Attorney, Agent, or Firm*—Joseph C. Gil; Carol Marmo

[57] ABSTRACT

The present invention provides a process for making 2-(methylthio)-5-(trifluoromethyl)-1,3,4-thiadiazole. The process includes the steps of reacting methyidithiocarbazinate with trifluoroacetic acid, in the absence of phosphorus trichloride, to form a mixture of 2-(methylthio)-5-(trifluoromethyl)-1,3,4-thiadiazole and 2,5-bis-(methylthio)-1,3,4-thiadiazole. Further, the process of the present invention includes selectively removing the 2,5-bis-(methylthio)-1,3,4-thiadiazole by acidifying the reaction mixture, and then separating the aqueous and organic phases.

17 Claims, No Drawings

PROCESS FOR MAKING 2-(METHYLTHIO)-5-(TRIFLUOROMETHYL)-1,3,4-THIADIAZOLE USING METHYLDITHIOCARBAZINATE WITH TRIFLUOROACETIC ACID WITH SELECTIVE REMOVAL OF 2,5-BIS (METHYLTHIO)-1,3,4-THIADIAZOLE

This application is a Continuation-in-Part of Ser. No. 08/989,563, filed Dec. 12, 1997.

TECHNICAL FIELD OF THE INVENTION

The field of this invention is the synthesis of thiadiazoles. More particularly, this invention pertains to an improved process for making 2-(methylthio)-5-(trifluoromethyl)-1,3,4-thiadiazole using trifluoroacetic acid and methyidithiocarbazinate; and selectively removing the 2,5-10 bis (methylthio)-1,3,4-thiadiazole. The selective removal of the 2,5-bis(methylthio)-1,3,4-thiadiazole is accomplished by acidifying the crude reaction product, and then separating the organic and aqueous phases.

BACKGROUND OF THE INVENTION

Existing methods for preparing 2-(methylthio)-5-(trifluoromethyl)-1,3,4-thiadiazole are limited by the excessive cost of commercial scale application of laboratory procedures. Many existing reports are based on laboratory studies and thus present little information on how reaction temperatures and particular reactants would affect product yield or purity. In addition, the use of procedures and reactions developed in the laboratory cannot be directly applied to commercial scale production because such laboratory procedures typically involve the use of expensive reactants and or expensive (e.g., separation and purification procedures) techniques.

U.S. Pat. No. 3,562,284 discloses a process for making certain 2-(alkylthio)-5-(halogenoalkyl)-1,3,4-thiadiazoles such as 2-(methylthio)-5-(trifluoromethyl)-1,3,4-thiadiazoles wherein methyidithio-carbazinate is reacted with a carboxylic anhydride (e.g., trifluoroacetic anhydride) or with a carboxylic acid (e.g., trifluoroacetic acid) in a solvent (e.g., toluene). The reaction can occur in the presence of phosphorous trichloride and pyridine with added sulfuric acid (DE-A-3,422,861) or with carbonyl chlorides (e.g., trifluoroacetyl chloride) and diethylene glycol dimethyl ether, as well as with pyridine and sulfuric acid (DE-A-3,722,320). The first-mentioned method is poorly suited for commercial, large-scale production because the reactants (anhydrides) are expensive and they are used in excess. In addition, by using an anhydride, only half of the reaction moiety is utilized. The reaction with carboxylic acids, phosphorus trichloride, pyridine, sulfuric acid and carbonyl chlorides requires an extensive work-up process in which the pyridine is separated off and recovered. Further, the use of phosphorus trichloride results in the formation of only sparingly soluble reaction products, which makes mixing difficult. Finally, the yields realized from such processes are unacceptably low.

Other procedures for making a 2-(substituted)-5-(trifluoromethyl)-1,3,4-thiadiazole involve the reaction of a carboxylic acid (e.g., trifluoroacetic acid) and a dithiocarbazic ester in the presence of a phosphorylchloride or polyphosphoric acid. (See, e.g., U.S. Pat. No. 5,162,539 and Gyoefi and Csavassy, Acta Chimica Academiae *Scientiarum Hungaricae. Tomus* 82 (1), (91–97, 1974). The use of such phosphorus compounds results in the formation of waste products containing unacceptably high levels of phosphates and, thus, creates an environmental hazard. Still further, this method requires the use of dry methyidithiocarbazinates (a toxic convulsant). In the dry state this material creates a severe industrial hygiene problem.

There is a need in the art, therefore, for an efficient, high yield, practical, safe method for the commercial, large-scale production of 2-(methylthio)-5-(trifluoromethyl)-1,3,4 thiadiazole. The present invention provides such a process.

BRIEF SUMMARY OF THE INVENTION

The present invention provides a process for preparing 2-(methylthio)-5-(trifluoromethyl)-1,3,4-thiadiazole. The process includes the steps of reacting methyldithiocarbazinate (MDTC) with trifluoroacetic acid (TFA), in the absence of phosphorus trichloride, to form a mixture of 2-(methylthio)-5-(trifluoromethyl)-1,3,4-thiadiazole (TDA) and 2,5-bis-(methylthio)-1,3,4-thiadiazole (bis by-product). Further, the process of the present invention includes selectively removing the bis by-product by acidifying the TDA and bis by-product mixture, and then separating the organic and aqueous phases.

The reaction of MDTC with TFA results in a mixture which comprises a first organic phase and a first aqueous phase. The excess TFA is contained within the first aqueous phase. The TDA and bis by-product are contained within the first organic phase. The first organic phase is separated from the first aqueous phase, and the first organic phase is then acidified with a concentrated inorganic acid. As a result of acidification, a second organic phase and a second aqueous phase are formed. Since the bis by-product is a stronger base than the TDA, selective quaternization of the bis by-product takes place. The quaternized bis by-product is soluble in the second aqueous phase of the mixture in the form of a quaternary ammonium salt. The second aqueous phase is separated from the second organic phase, and the quaternized bis by-product, in the form of a quaternary ammonium salt, remains in the second aqueous phase.

The reaction mixture is acidified with a concentrated inorganic acid such as hydrochloric acid, sulfuric acid or nitric acid. The use of sulfuric acid is preferred. The sulfuric acid has a concentration of from about 55% to about 95% and, preferably about 70%. Where 70% sulfuric acid is used, the amount of sulfuric acid added to the reaction mixture is from about 2 moles to about 10 moles of sulfuric acid per mole of the 2,5-bis-(methylthio)-1,3,4-thiadiazole and, preferably from about 4 moles to about 7 moles of sulfuric acid per mole of the 2,5-bis-(methylthio)-1,3,4-thiadiazole.

Acidification typically occurs at a temperature of from about 10° C. to about 60° C., preferably from about 20° C. to about 40° C. and, more preferably from about 25° C. to about 300° C.

The reaction of methyldithiocarbazinate with trifluoroacetic acid can occur in the presence of a solvent. The solvent can be the trifluoroacetic acid itself or an aprotic, aromatic solvent such as toluene, xylene, cumene or mesitylene. Toluene is preferred.

Any suitable ratio of methyldithiocarbazinate and trifluoroacetic acid can be used. Either reactant can be present in a molar excess. Thus the molar ratio of methyidithiocarbazinate to trifluoroacetic acid can range from about 4:1 to about 1:5. Where methyldithiocarbazinate is present in a molar excess, a preferred molar ratio of methyldithiocarbazinate to trifluoroacetic acid is from about 2:1 to about 1.5:1. Where trifluoroacetic acid is present in a molar excess, a preferred molar ratio of methyldithiocarbazinate to trifluoroacetic acid is from about 1:1.25 to about 1:2.

DETAILED DESCRIPTION OF THE INVENTION

I. The Invention

The present invention provides a novel process for preparing 2-(methylthio)-5-(trifluoromethyl)-1,3,4-thiadiazole (TDA), an intermediate useful in the preparation of herbicides. The novel process of this invention uses methyidithiocarbazinate (MDTC) and trifluoroacetic acid (TFA) as the primary reactants. The MDTC and TFA are reacted in the absence of phosphorus trichloride. The process allows for production of TDA in high yields with efficient means for removing by-products and recycling key reagents. More particularly, the process includes selective removal of the 2,5-bis(methylthio)-1,3,4-thiadiazole by acidification of the TDA and bis by-product mixture, followed by phase separation.

II. Process Using Excess Trifluoroacetic Acid

In one aspect, a process of the present invention for preparing 2-(methylthio)-5-(trifluoromethyl)-1,3,4-thiadiazole includes the steps of reacting methyldithiocarbazinate in a solvent with an excess of trifluoroacetic acid, and removing water and excess trifluoroacetic acid.

MDTC prepared by any means can be used in the present process. Especially preferred means for preparing MDTC are disclosed in U.S. patent application Ser. No. 08/743,763, 08/743,764 and 08/743,775, all filed on Nov. 7, 1996. The disclosures of all those patent applications are incorporated herein by reference. TFA is commercially available.

MDTC is reacted with a molar excess of TFA. As used herein, the phrase "molar excess" means that the moles of TFA exceed the moles of MDTC in the reaction. TFA is preferably present at a 10 to 500 percent molar excess relative to MDTC. That is, the molar ratio of TFA to MDTC (TFA:MDTC) is from about 1.1:1 to about 5:1. More preferably, the TFA:MDTC molar ratio is from about 1.25:1 to about 2.5:1 and, even more preferably from about 1.25:1 to about 2:1. As shown hereinafter in the Examples, increasing the molar excess of TFA relative to MDTC significantly and substantially increases the yield of TDA.

The reaction preferably occurs at a temperature of from about 30° C. to about 150° C. and, more preferably from about 30° C. to about 140° C. Where the temperature is from about 80° C. to about 130° C., reaction time is from about 1 to about 5 hours.

The MDTC used in the present process can contain water. The ability to use "wet" MDTC offers a substantial benefit over existing processes that use only dry MDTC. MDTC is a known toxic substance and its use in dry form is likely to result in contamination of the air in processing plants with MDTC dust. This environmental hazard is substantially reduced where wet MDTC can be used. For use in the present process, MDTC can contain up to about 10 weight percent water.

Further, unlike existing processes, water can be added as a separate reactant. The total amount of water in the reaction mixture is preferably less than about 30 grams of water per 0.5 moles of MDTC. As shown hereinafter in the Examples, the presence of 30 or less grams of water per 0.5 moles of MDTC has no deleterious effect on product formation. Increasing the amount of water to 40 grams or more resulted in reductions in product (TDA) yield.

The reaction of TFA and MDTC occurs in the presence of a solvent. In one embodiment, the trifluoroacetic acid itself serves as the solvent. Preferably, however, an aprotic, aromatic solvent is used. Such solvents are well known in the art. Exemplary and preferred such aprotic, aromatic solvents are toluene, xylene, cumene and mesitylene. Toluene is especially preferred.

The amount of solvent used can vary over a wide range as readily determined by a skilled artisan. Where an aprotic, aromatic solvent is used, it is present in an amount of from about 0.5 moles to about 3.5 moles of toluene per mole of MDTC. Preferably, toluene is present in an amount of from about 1.5 moles to about 3.0 moles per mole of MDTC and, more preferably in an amount of from about 2.5 to about 3.0 moles of toluene per mole of MDTC.

The reaction can proceed by mixing the entire desired amounts of MDTC and TFA. All other modes of addition are suitable as well.

The reaction mixture of MDTC and TFA can optionally include a catalyst. An exemplary and preferred catalyst is p-toluene sulfonic acid. Where p-toluene sulfonic acid is used, it is present in an amount of about 2.0 grams per mole of MDTC.

Water is formed as a reaction product of the TFA and MDTC reaction. Additional water may also be present because of recycle streams. Water is removed from the reaction mixture by an azeotropic distillation. The azeotropic removal of water is readily accomplished in the presence of the solvent, particularly where toluene is used as a co-solvent. The temperature required for the completion of the reaction is adequate for the azeotropic removal of the water and removal of the excess trifluoroacetic acid. Therefore, no additional work-up is required.

III Removal of Bis-Thiadiazole

In another aspect, the present invention provides a process for preparing TDA, which process includes the steps of (i) reacting MDTC with TFA, in the absence of phosphorus trichloride, to form a mixture of TDA and 2,5-bis-(methylthio)-1,3,4-thiadiazole, (the bis by-product); (ii) selectively removing the bis by-product by acidification of the reaction mixture; and (iii) separating the organic and aqueous phases. Reaction temperatures for the reaction of MDTC and TFA are the same as set forth above.

Any suitable ratio of MDTC and TFA can be used. Either reactant can be present in a molar excess. Thus the molar ratio of MDTC to TFA can range from about 4:1 to about 1:5. Where MDTC is present in a molar excess, a preferred molar ratio of MDTC to TFA to is from about 2:1 to about 1.5:1. Where TFA is present in a molar excess, a preferred molar ratio of MDTC to TFA is from about 1:1.25 to about 1:2.0. The amount of the bis by-product produced from the reaction of MDTC and TFA decreases as the ratio of MDTC to TFA decreases.

As set forth above, the reaction of MDTC with TFA preferably occurs in the presence of a solvent. Preferred solvents are the same as set forth above. Toluene is most preferred.

The reaction of MDTC with TFA, in the absence of phosphorus trichloride, forms a mixture consisting of a first aqueous phase and a first organic phase. The excess TFA is contained in the first aqueous phase, and the TDA and bis by-product are contained in the first organic phase. The first organic phase is separated from the first aqueous phase, and the first organic phase is then acidified with a concentrated inorganic acid. As a result of acidification, a second organic phase and a second aqueous phase are formed. Since the bis by-product is a stronger base than the TDA, selective quaternization of the bis by-product takes place. The quaternized bis by-product is soluble in the second aqueous phase in the form of a quaternary ammonium salt. The second aqueous phase is separated from the second organic phase, and the quaternized bis by-product, in the form of a quaternary ammonium salt, remains in the second aqueous phase.

The reaction mixture is acidified with a concentrated inorganic acid such as hydrochloric acid (HCl), sulfuric acid ($H_2SO_4$) or nitric acid ($HNO_3$). Preferably, the acid has a pKa of from about 1 to about 4. The use of sulfuric acid is preferred. The sulfuric acid has a concentration of from about 55% to about 95% and, preferably about 70%. Where 70% sulfuric acid is used, the amount of sulfuric acid added to the reaction mixture is from about 2 moles to about 10 moles of sulfuric acid per mole of the bis-byproduct and, preferably from about 4 moles to about 7 moles of sulfuric acid per mole of the bis-byproduct. Acidification typically occurs at a temperature of from about 10° C. to about 60° C., preferably from about 20° C. to about 40° C. and, more preferably from about 25° C. to about 30° C.

The following Examples illustrate preferred embodiments of the present invention and are not limiting of the specification or claims in any way.

EXAMPLES

Example 1

Production of 2-(methylthio)-5-(trifluoromethyl)-1,3,4-thiadiazole (TDA) Using MDTC and Excess TFA A. General Protocol—Toluene (125 grams) was charged to a flask. 67.9 grams (0.5 moles) of methyldithiocarbazinate (MDTC) (90% A.I. with 5% water and 5% impurities) was added to the flask to form a mixture. Trifluoroacetic acid (TFA) (114 grams, 1.0 mole) was added to the mixture with agitation over 10 to 15 minutes without cooling. The temperature of the mixture rose to about 38° C. upon TFA addition.

The mixture was heated to about 70° C. and maintained at that temperature for about 3 hours. The mixture was then heated to reflux (about 115° C.–116° C.) to remove water and any distillable TFA. This temperature was maintained for about 10 minutes until no aqueous phase separates from the condensate. The yield of TDA was about 90% to 93%.

B. Effects of Excess TFA—The reaction of MDTC and TFA was carried out as set forth above in (A) except that the amount of TFA relative to MDTC was varied. TDA yields were determined at each TFA level. The results are summarized below in Table 1.

TABLE 1

Effect of TFA Excess on TDA Yield
(2.7 moles toluene/mole MDTC)

| TFA Excess, % | Net Yield, % | % Bis-by-product (Solvent Free) |
|---|---|---|
| 0 | 70.4 | 9.8 |
| 10 | 81.5 | 9.4 |
| 20 | 88.2 | 6.2 |
| 30 | 90.2 | 5.5 |
| 40 | 91.0 | 4.3 |
| 50 | 91.1 | 3.8 |
| 100 | 92.2 | 1.9 |
| 200 | 92.8 | 1.2 |

It can be seen from the data in Table 1 that increasing the molar excess of TFA increased the yield of TDA. The greatest increases in TDA yield were seen when the molar excess of TFA increased from 10% to about 100%. Increases in the molar excess of TFA from about 100% to about 200% resulted in only small gains in TDA yield.

C. Effects of Toluene as a Solvent—TDA was prepared in accordance with paragraph (A) above except that the level of toluene relative to the level of MDTC was varied. For these studies, 2 moles of TFA were reacted with one mole of MDTC. Summary data are shown in Table 2, below.

TABLE 2

Effect of Toluene on TDA Yield
2.0 moles TFA/mole MDTC

| Moles Toluene/Moles MDTC | % TDA net yield based on MDTC |
|---|---|
| 2.70 | 92.2 |
| 2.05 | 89.6 |
| 1.35 | 87.8 |
| 0.67 | 86.2 |

The data in Table 2 show that TDA yield increases with increasing levels of toluene. TDA yield did not improve substantially when toluene levels exceeded about 2.7 moles per mole of MDTC.

D. Effects of Water Levels—Water can be expected in the primary reaction from two main sources. First, the MDTC used in the reaction can contain up to about 10 weight percent water. Second, water can be added to enhance the recovery of TFA. Therefore, the effect of water on TDA recovery was studied. For these studies, 2.0 moles of TFA were reacted with one mole of MDTC. 2.1 moles of toluene per mole of MDTC were used. Results of these studies are shown below in Table 3.

TABLE 3

Effect of Water on the TDA Yield

| gms water added (0.5M batch) | TDA net yield % based on MDTC |
|---|---|
| 0 | 92.0 |
| 10 | 91.8 |
| 20 | 91.9 |
| 30 | 91.6 |
| 35 | 89.2 |
| 40 | 88.7 |
| 50 | 83.7 |

The data in Table 3 show that the presence of up to 60 grams of water per mole of MDC in the reaction medium did not adversely affect TDA net yields. When 1.5 moles of TFA were reacted with one mole of MDTC, however, a perceptible drop in TDA net yields was noticed at water levels of 30–40 grams of water per mole of MDTC (See Table 4).

TABLE 4

Effect of Water on TDA Yield

| gms water added (0.5M batch) | TDA net yield % based on MDTC |
|---|---|
| 0 | 91.1 |
| 10 | 90.6 |
| 15 | 90.1 |
| 20 | 89.3 |
| 30 | 87.5 |
| 35 | 84.2 |
| 40 | 83.1 |

Example 2
Reduction of Bis By-Product Levels

The main by-product that results from the reaction of MDTC with TFA is 2,5-bis-(methylthio)-1,3,4-thiadiazole (bis by-product). The bis by-product can be removed via acidification of the reaction mixture with a concentrated inorganic acid, followed by phase separation. The effects of acidification on bis by-product removal and TDA yield were examined as follows. Following the reaction of TFA with MDTC, the reaction mixture was cooled to a temperature of about 25° C. to 30° C. The reaction mixture consisted of a first aqueous phase and a first organic phase. The first aqueous phase was separated from the first organic phase. The excess TFA was recovered from the first aqueous phase. The TDA and bis by-product were contained within the first organic phase. About 5 moles of 70% $H_2SO_4$ per mole of removable bis by-product was then added to the first organic phase, resulting in the formation of a second aqueous phase and a second organic phase. The bis by-product was soluble in the second aqueous phase in the form of a quaternary ammonium salt. The second aqueous phase was separated from the second organic phase. The quaternized bis by-product in the form of a quaternary ammonium salt remained in the second aqueous phase.

Data from Table 1, above, show that the production of the bis by-product is dependent upon the molar excess of TFA used in the initial reaction. The production of the bis by-product decreases as the molar excess of TFA relative to MDTC increases. For subsequent studies, the molar ratio of TFA to MDTC was 1.5:1.

Data from the following two tables (Tables 5 & 6) demonstrates the effect of temperature and agitation on the removal of bis by-product vis-a-vis recovery of TDA.

TABLE 5

| Temp ° C. | Mol 70% $H_2SO_4$/Mol "bis-sulfide" | Solvent-free "bis-sulfide" before $H_2SO_4$ treatment | Sovent-free "bis-sulfide" after $H_2SO_4$ treatment | % Net TDA Recovery |
|---|---|---|---|---|
| Set I With PPP 6-25-0128 | | | | |
| Ambient (25°) | 6.0 | 2.21% | 0.17% | 99.5 |
| 40° C. | 6.0 | 2.21% | 0.22% | 99.1 |
| 50° C. | 6.5 | 2.21% | 0.24% | 98.9 |
| 60° C. | 6.5 | 2.21% | 0.31% | 98.6 |
| Set II with PPP 6-25-0130 | | | | |
| 30° C. | 6.0 | 2.16% | 0.22% | 99.6 |
| 50° C. | 6.0 | 2.16% | 0.29% | 99.0 |
| 70° C. | 6.0 | 2.16% | 0.38% | 98.3 |
| Repeat 70° C. | 6.0 | 2.16% | 0.39% | 98.4 |

TABLE 6

"Bis" Removal from TDA/Tol (6 Moles $H_2SO_4$ per Mole of Removable "Bis")

| Temp ° C. | RPM (agitation) | % "Bis" zero time | % "Bis" 5 mts | % "Bis" 10 mts | % "Bis" 15 mts | % "Bis" 20 mts | % "Bis" 25 mts | % "Bis" 30 mts | % "Bis" 35 mts | % "Bis" 40 mts |
|---|---|---|---|---|---|---|---|---|---|---|
| 50 | 100 | 0.543 | 0.367 | 0.333 | 0.265 | 0.210 | — | 0.134 | — | 0.085 |
| 50 | 300 | 0.543 | 0.103 | 0.039 | 0.015 | 0.017 | 0.017 | 0.014 | 0.025 | 0.019 |
| 30 | 300 | 0.543 | 0.053 | 0.017 | — | Zero | — | zero | — | zero |

Studies showed that up to 10 moles of 70% $H_2SO_4$ per mole of the bis by-product could be used at 25° C. to 30° C. for the selective removal of the bis by-product. With a solution of about 40% TDA and 60% toluene, 5 moles of 70% $H_2SO_4$ per mole of the bis by-product reduced bis by-product levels on a solvent-free basis to about 0.1%. With a solution of about 60% TDA and 40% toluene, 4 moles of 70% $H_2SO_4$ per mole of bis by-product reduced bis by-product levels on a solvent-free basis to about 0.1%.

In both cases, an additional 2 to 3 moles of 70% $H_2SO_4$ appeared to be necessary to reduce the bis by-product to undetectable levels. Such. attempts, however, resulted in TDA losses ranging from 2–3%. It was difficult to reduce bis by-product levels to below about 0.1% even with 8 to 10 moles of 70% $H_2SO_4$ per mole of bis by-product at 60° C. to 70° C. Under such conditions, TDA losses ranged from 5–8%.

Thus, a practical approach is to reduce bis by-product levels to about 0.1%, on a solvent-free basis, by using about 4–5 moles of 70% $H_2SO_4$ per mole of bis by-product at a temperature of about 250° C. to 30° C.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process of making 2-(methylthio)-5-(trifluoromethyl)-1,3,4-thiadiazole comprising the steps of:
   (a) reacting methyldithiocarbazinate with trifluoroacetic acid in the absence of phosphorus trichloride to form a mixture of 2-(methylthio)-5-(trifluoromethyl)-1,3,4-thiadiazole and 2,5-bis-(methylthio)-1,3,4-thiadiazole, wherein the molar ratio of methyldithiocarbazinate to trifluoroacetic acid is from about 4:1 to about 1:5, and wherein the mixture contains a first organic phase and a first aqueous phase;
   (b) separating the first organic phase and the first aqueous phase;

(c) acidifying the first organic phase with a concentrated inorganic acid, resulting in the formation of a second organic phase and a second aqueous phase, wherein the 2,5-bis-(methylthio)-1,3,4-thiadiazole is soluble in the second aqueous phase; and (d) separating the second organic phase and the second aqueous phase, wherein the 2,5-bis-(methylthio)-1,3,4-thiadiazole remains in the second aqueous phase.

2. The process of claim 1 wherein the concentrated inorganic acid is hydrochloric acid, sulfuric acid or nitric acid.

3. The process of claim 2 wherein the concentrated inorganic acid is sulfuric acid.

4. The process of claim 3 wherein the sulfuric acid has a concentration of from about 55% to about 95%.

5. The process of claim 4 wherein the sulfuric acid has a concentration of about 70%.

6. The process of claim 5 wherein the amount of sulfuric acid added to the reaction mixture is from about 2 moles to about 10 moles of sulfuric acid per mole of the 2,5-bis-(methylthio)-1,3,4-thiadiazole.

7. The process of claim 6 wherein the amount of sulfuric acid added to the reaction mixture is from about 4 moles to about 7 moles of sulfuric acid per mole of the 2,5-bis-(methylthio)-1,3,4-thiadiazole.

8. The process of claim 1 wherein acidification occurs at a temperature of from about 20° C. to about 60° C.

9. The process of claim 8 wherein acidification occurs at a temperature of from about 20° C. to about 40° C.

10. The process of claim 9 wherein acidification occurs at a temperature of from about 25° C. to about 30° C.

11. The process of claim 1 wherein the reaction occurs in the presence of a solvent.

12. The process of claim 11 wherein the solvent is trifluoroacetic acid.

13. The process of claim 11 wherein the solvent is an aprotic, aromatic solvent.

14. The process of claim 13 wherein the aprotic, aromatic solvent is toluene, xylene, cumene or mesitylene.

15. The process of claim 14 wherein the aprotic, aromatic solvent is toluene.

16. The process of claim 1 wherein the molar ratio of methyidithiocarbazinate to trifluoroacetic acid is from about 2:1 to about 1.5:1.

17. The process of claim 16 wherein the molar ratio of methyldithiocarbazinate to trifluoroacetic acid is from about 1:1.25 to about 1:2.5.

* * * * *